US00PP07986P

United States Patent [19]

Carruth

[11] Patent Number: Plant 7,986

[45] Date of Patent: Sep. 29, 1992

[54] HYBRID MINIATURE ROSE PLANT NAMED WEKHELEN

[75] Inventor: Thomas F. Carruth, Altadena, Calif.

[73] Assignee: Weeks Wholesale Rose Grower, Inc., Upland, Calif.

[21] Appl. No.: 651,752

[22] Filed: Feb. 7, 1991

[51] Int. Cl.[5] ..... A01H 5/00

[52] U.S. Cl. ..... Plt./7.1

[58] Field of Search ..... Plt. 7, 7.1, 9

*Primary Examiner*—Howard J. Locker

*Attorney, Agent, or Firm*—Christie, Parker & Hale

[57] ABSTRACT

A new hybrid miniature rose for garden decoration, characterized by a profusion of well-formed mossed flowers of apricot orange coloration and moss fragrance of sweet juniper on the buds.

1 Drawing Sheet

BACKGROUND OF THE INVENTION

This invention relates to a new and distinct variety of hybrid miniature rose. The plant is dwarf, bushy, compact and may be grown outdoor for garden decoration. It has as its seed parent the variety known as 'Fairy Moss' (U.S. Plant Pat. No. 3,083) and as pollen parent the variety known as 'Macnewye' (U.S. Plant Pat. No. 5,428). The varietal denomination of the new variety of 'Wekhelen'.

SUMMARY OF THE INVENTION

Among the features which distinguish the new variety from other cultivars are the following combination of characteristics: profusion of well-formed mossed flowers of apricot coloration (an unusual color among moss roses), moss fragrance of sweep juniper on the buds, profusion of prickles, above average resistance to powdery mildew when compared to other moss roses and a full rounded bushy growth habit. 'Wekhelen' may be propagated by cuttings, budding, grafting and tissue culture.

Asexual propagation of the new variety as performed in Kern County and Upland, Calif., shows that the foregoing and other distinguishing characteristics come true to form and are established and transmitted through succeeding propagations.

COMPARISON WITH PARENT VARIETIES

The new rose may be distinguished from its seed parent, 'Fairy Moss' by the following combination of characteristics: whereas 'Wekhelen' bears flowers of apricot orange coloration, 'Fairy Moss' bears flowers of a pure pink coloration. The flowers of 'Fairy Moss' are single (5 to 8 petals), whereas the new cultivar bears flowers with significantly higher petalage (28 to 34 petals). Whereas 'Wekhelen' is a vigorous, bushy, rounded plant, the seed parent is significantly less vigorous, yielding an overall smaller, less filled plant at maturity.

The new variety may be distinguished from its pollen parent. 'Macnewye' by the following combination of characteristics: whereas the pollen parent is classified as a Grandiflora, the new rose is of significantly smaller size in flower, foliage and growth habit, and is classified as a miniature. 'Wekhelen' is a moss rose, whereas 'Macnewye' has none of the moss rose characteristics.

BRIEF DESCRIPTION OF THE ILLUSTRATION

The accompanying photograph illustrates the plant in color and shows the flowering thereof from bud to full bloom depicted in color as nearly correct as it is possible to make in an illustration of this character. Throughout this description, color names and values are based upon the Colour Chart of The Royal Horticultural Society of London, England, except where common terms of color definition are employed.

DESCRIPTION OF THE NEW VARIETY

The following description pertains to rose plants of the new cultivar grown outdoors in October, 1990 in Upland, Calif. and is believed to apply to plants of the variety grown elsewhere in similar conditions of soil and climate.

FLOWER

The new variety bears its flowers usually singly, sometimes three or more per stem. Flowers are borne in irregular rounded clusters on normal strength, medium long, stems, for the class. Outdoor the plant blooms very abundantly and nearly continuously during the growing season. The flower buds have a moderately strong moss fragrance of sweet juniper.

BUD

The peduncle is of an average to long length for the class, of average caliper, and usually erect. It is very rough, with numerous stipitate glands, numerous hairs and small prickles. Peduncle color is between Yellow-Green 144B and Green 138B.

Before the calyx breaks, the bud is of medium to large size for the class, moderately long in length, and pointed to ovoid in shape. The surface of the bud bears the moss characteristics of numerous stipitate glands and many hairs. Usually, slender foliaceous parts extend beyond the tip of the bud equal to ⅓ or more of its length. Bud color is between Yellow-Green 144A and Green 138B.

The inner surface of the sepals is lined with very short, fine, woolly tomentum; sepal margins are lined with many hairs and some stipitate glands.

As the first petals open, the bud is medium to large for the class, medium long in length, and somewhat pointed to ovoid in form. The color of the outside surface of the newly opened petals is between Red 43B and Orange-Red 35B, with a moderately broad zone at the base of the petal of near Yellow 6B. The color of the inside surface of the newly opened petals is between Orange-Red 33B and Orange-Red 31C, with a broad zone at the base of the petal of between Yellow 6A and Yellow 8A. The bud opens up well and is not prevented from opening in cold, hot or dry weather conditions.

BLOOM

When fully open, the bloom is moderately large for the class, ranging from 5 to 6 cms. in diameter. Petalage is double with 28 to 34 petals and 1 to 4 petaloids arranged irregularly. When partially open, the bloom form is somewhat flat and full to high centered, and the petals are moderately spiraled to undulated with petal edges somewhat rolled outward. When fully open, the bloom form is more cupped, and the petals are somewhat loosely cupped to undulated with petal edges more reflexed outward.

PETALS

The petals are of moderately heavy substance and of moderate thickness, with inside surfaces moderately shiny to satiny and outside surfaces somewhat shiny. The outside petals are nearly round in shape with somewhat mucronate apices. The inside petals are nearly round to broadly obovate in shape with slightly mucronate apices.

The following description and color values are from observations of flowers on a plant grown outdoor in Upland, Calif. in the month of October. Colors may be modified by being shaded or tinted with other colors.

NEWLY OPENED FLOWER

The outside surface of the outside petals is between Red 41B and Orange-Red 35C, with a moderately broad zone at the base of the petal between Yellow 13C and Yellow-Orange 16B in color. The inside surface of the outside petals has a broad zone at the base of the petal between Yellow 13C and Yellow-Orange 16B in color that suffuses to between Orange-Red 31B and Orange-Red 31D approaching the petal edge. At the petal edge the color can sometimes be washed with between Red 49A and Red 49B.

The outside surface of the intermediate and inner petals is between Red 41B and Orange-Red 35C, with a moderately broad zone at the base of the petal between Yellow 13C and Yellow-Orange 16B in color. The inside surface of the intermediate and inner petals has a broad zone at the base of the petal between Yellow 16C and Yellow-Orange 16B in color that suffuses to between Orange-Red 31B and Orange-Red 31D approaching the petal edge. There is usually no washing of color at the edge of the petal.

The general color tonality of the newly opened flower is between Orange-Red 31B and Orange-Red 31D, sometimes washed with between Red 49A and Red 49B on the outer petal edges.

THREE DAY OLD FLOWER

The outside surface of the outside and inner petals is between Red 41D and Orange-Red 35D, with a moderately broad zone at the base of the petal between Yellow-Orange 14C and Yellow-Orange 16C in color. The inside surface of the outside and inner petals has a broad zone at the base of the petal between Yellow-Orange 14C and Yellow-Orange 16C. A broad portion of the petal is washed with between Red 50D and Red 49C in color.

The general color tonality of the three day old flower is between Red 50D and Red 49C with a central "eye" zone of between Yellow-Orange 14C and Yellow-Orange 16C.

On the spent bloom, the petals usually drop off cleanly. In October, blooms on the bush growing in the garden generally last from four to five or more days. Cut roses from plants grown outdoor and kept at normal indoor room temperatures generally last form four to five or more days.

MALE REPRODUCTIVE ORGANS

Stamens are average to many in number and are arranged regularly about the pistil. The filaments are irregular in length, most with anthers. The anthers are moderately large for the class and all open approximately at the same time. Anther color is near Yellow-Orange 16A when immature and near Yellow-Orange 16C at maturity. Pollen is very abundant and between Yellow-Orange 15C and Yellow-Orange 16A in color.

FEMALE REPRODUCTIVE ORGANS

Pistils are average to many in number (approximately 60). The styles are moderately uneven, moderately short in length, average in caliper, and somewhat bunched. Stigma color is near Yellow 8B. Ovaries are usually all enclosed in the calyx.

Hips on this variety when grown in Upland, Calif. are average in length, very ovoid to globular in form, and near Orange 28A in color. The hip surface is very prickly and glandular with moderately thick fleshy walls. The sepals fall quickly. Seeds are average to many in number (approximately 15 to 20), and usually somewhat medium to large in size.

FOLIAGE

The compound leaves are usually comprised of three to five leaflets and are borne abundantly. The leaves are somewhat medium to large for the class, very heavy to leathery in texture, and moderately semi-glossy in finish. The leaflets are shaped moderately oval with somewhat acute to acuminate apices and moderately round bases. Their margins are usually simply serrate to irregular.

The upper surface of the mature leaf is between Yellow-Green 147A and Green 133A. The undersurface of the mature leaf is between Green 137C and Greyed-Green 191B. The upper surface of the young leaf is between Yellow-Green 147A and Green 136B, sometimes moderately suffused with between Greyed-Purple 183C and Greyed-Purple 184C. The undersurface of the young leaf is near between Green 137C and Greyed-Green 191B, sometimes lightly suffused with between Greyed-Purple 183C and Greyed-Purple 184C.

The rachis is average to heavy caliper and moderately rough and grooved with many stipitate glands and some hairs on the upper side. The underside of the rachis is somewhat rough with some stipitate glands and prickles.

The stipules are moderately long, medium in width with moderately long straight points that sometime turn out at an angle of less than 45 degrees.

The plant displays an above average degree of resistance to powdery mildew and rust as compared to other commercial varieties of the moss bloodline grown under comparable conditions in Upland, Calif.

GROWTH

The plant is of dwarf, bushy, compact habit; medium height for the class with very full branching. 12 to 16 inches at maturity. It displays moderately vigorous growth and the canes are somewhat medium to heavy caliper for the class.

The major stems are between Yellow-Green 146C and Green 138B, with some bark formation of near Greyed-Orange 177C. They bear some large prickles which are somewhat long for the class. The large prickles are almost straight, hooked slightly downward with a medium length somewhat narrow base; prickle color is near Greyed-Orange 177C. The major stem bears many small prickles and some coarse hairs which are near Greyed-Orange 177C in color.

The branches are between Yellow-Green 144B and Green 138B. They bear many large prickles which are somewhat long for the class. The large prickles are almost straight but hooked slightly downward with a medium length, somewhat narrow base. The branches bear many small prickles and coarse hairs. Prickle color is between Greyed-Red 180C and Greyed-Orange 171D.

The new shoots are between Yellow-Green 144B and Green 138B, often somewhat heavily suffused with near Greyed-Purple 183D. They bear many large prickles which are somewhat long for the class. The large prickles are almost straight, hooked slightly downward with a medium length somewhat narrow base. The shoots bear many small prickles and coarse hair. Prickle color is near Greyed-Orange 164C, sometimes lightly washed with near Greyed-Purple 183D.

I claim:

1. A new and distinct variety of hybrid miniature rose plant substantially as shown and described.

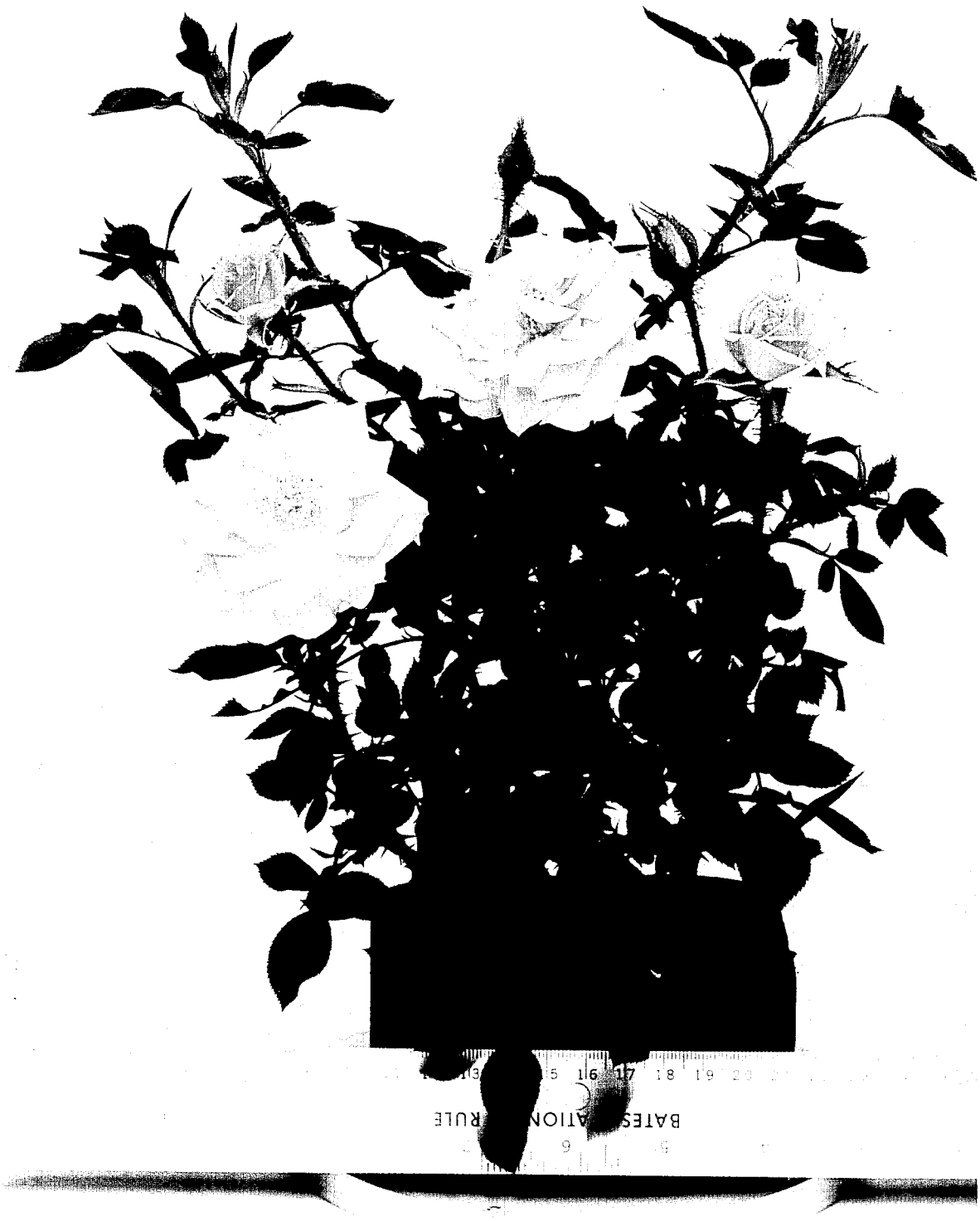

* * * * *